United States Patent [19]

Laney

[11] Patent Number: 5,800,804
[45] Date of Patent: *Sep. 1, 1998

[54] O-ACYL SERINES AND THREONINES AS DEODORANTS

[75] Inventor: Judith Wolfe Laney, Silver Spring, Md.

[73] Assignee: The Gillette Company, Boston, Mass.

[*] Notice: The term of this patent shall not extend beyond the expiration date of Pat. No. 5,431,904.

[21] Appl. No.: 617,424

[22] Filed: Mar. 18, 1996

Related U.S. Application Data

[63] Continuation-in-part of Ser. No. 562,086, Nov. 22, 1995, Pat. No. 5,648,513, which is a continuation of Ser. No. 428,706, Apr. 25, 1995, abandoned, which is a continuation of Ser. No. 118,188, Sep. 9, 1993, Pat. No. 5,431,904.

[51] Int. Cl.[6] ............................. A61K 7/32; A61K 7/00
[52] U.S. Cl. .......................... 424/65; 424/400; 424/401
[58] Field of Search ............................. 424/65, 400, 401

[56] References Cited

U.S. PATENT DOCUMENTS

| | | |
|---|---|---|
| 3,107,252 | 10/1963 | Lubowe . |
| 4,089,942 | 5/1978 | Bore et al. ........................ 424/47 |
| 5,213,791 | 5/1993 | Lyon et al. ........................ 424/65 |
| 5,431,904 | 7/1995 | Laney ........................ 424/65 |

FOREIGN PATENT DOCUMENTS

| | | |
|---|---|---|
| 7-179328 | 7/1995 | Japan . |
| 348210 | 12/1967 | Russian Federation . |
| 592631 | 9/1947 | United Kingdom . |
| 1446584 | 8/1976 | United Kingdom . |
| 95/07069 | 3/1995 | WIPO . |

OTHER PUBLICATIONS

Bore et al., Chem. Abs., No. 87(16):122645f (1977).
Hirata et al., Chem. Abs., No. 113(8):64563v (1989).
Inoue, Chem. Abs., No. 111(16):140544r (1988).
Klosa, Chem. Abs., No. 78(13):84815r (1973).
Mitomo, Chem. Abs., No. 83(4):32923h (1975).
Ono et al., Chem. Abs., No. 108(22):188398m (1987).
Sagarin, Cosmetics Science and Technology, pp. 717, 733 and 1202–1211 (1957).
Sato et al., Chem. Abs., No. 110(16):141224c (1987).
Takasago Perfumery Co., Ltd., Chem. Abs., No. 103(24):200711g (1985).

Primary Examiner—Shelley A. Dodson
Attorney, Agent, or Firm—Stephan P. Williams

[57] ABSTRACT

The invention relates to a method for reducing malodor, preferably by generating a pleasant odor, in the axilla utilizing a deodorant composition containing a competitive substrate for the malodor producing enzyme. Upon cleavage by the malodor producing enzyme, the compounds of the present invention result in byproducts which produce either a neutral or a pleasant odor. The compound is present in a dermatologically acceptable vehicle, and in an amount effective to produce either a neutral or a pleasant odor. The present invention also relates to novel O-acylated serine and threonine compounds and method for the production thereof.

12 Claims, No Drawings

O-ACYL SERINES AND THREONINES AS DEODORANTS

RELATED APPLICATIONS

The present application is a continuation-in-part of application Ser. No. 08/562,086, filed on Nov. 22, 1995, now U.S. Pat. No. 5,648,513, which application was a continuation of application Ser. No. 08/428,706, filed on Apr. 25, 1995, now abandoned, which application was a continuation of application Ser. No. 08/118,188, filed on Sep. 9, 1993, now U.S. Pat. No. 5,431,904.

BACKGROUND OF THE INVENTION

The present invention relates to deodorants, a method of producing a pleasant odor in the axilla, compounds useful as deodorants and method for the production thereof.

The eccrine and apocrine sweat glands are the structures of the human body responsible for sweat. The apocrine glands become active at puberty and produce an odorless proteinaceous secretion. Axillary bacteria act on the apocrine secretions to produce the pungent odor known as axillary malodor.

Current deodorants are generally of three types: odor maskers, antiperspirants, and germicides. Despite the many disclosures in the art pertaining to deodorant compositions, current products are not sufficient to suppress odor in a significant proportion of the population, particularly during periods of "stress." There thus remains a need in the art for new deodorant compositions and methods which are effective, safe and economical.

OBJECTS AND SUMMARY OF THE INVENTION

In view of the above, an object of the present invention is to provide new deodorant compositions which are effective, safe and economical. It is also an object of the invention to provide deodorant compositions which result in the production of a pleasant odor in the axilla, particularly during periods of "stress." A further object of the present invention is to provide a method of producing a pleasant odor and/or of suppressing odor employing the deodorant compositions of the invention.

The present invention thus relates to a deodorant composition comprising a compound which is capable of serving as an alternative substrate to the naturally occurring malodor producing precursor. The compound is present in a dermatologically acceptable vehicle, and in an amount effective to produce a pleasant odor.

The present invention further relates to methods of using the deodorant compositions of the present invention to prevent malodor. Such methods include producing a pleasant odor. In some instances, for example, with the O-acyl serines, not only is a pleasant odor produced, but body malodor is also suppressed upon application to the skin of the deodorant composition of the present invention.

The present invention also relates to novel O-acylated serine and threonine compounds, and a method for their production.

DETAILED DESCRIPTION OF THE INVENTION

The current invention provides a novel deodorant composition. In accordance with the invention, a pleasant odor is produced by the topical application of compounds which are cleaved by the malodor-forming enzyme and thus compete with the naturally occurring malodor producing precursor. The compounds are O-acylated serine and threonine derivatives. Deodorant compositions comprising at least one compound from the specified group of O-acylated serine and threonine derivatives in an effective concentration will result in the production of a pleasant odor when applied to the underarm. In many cases, not only is a pleasant odor produced, but the production of axillary malodor is suppressed. Tests indicate that these compositions significantly attenuate the body odors formed in the axilla.

Axillary malodor is generated by certain skin bacteria in the presence of apocrine secretion. Two strains of bacteria which produce axillary malodor when incubated with human apocrine secretions are Staphylococcus and several Coryneform isolates. Production of human axillary malodor can be assayed from these strains of bacteria by incubating cells with apocrine secretions collected from human axilla that has been sterilized in a phosphate buffer at pH 6.8. The volatile malodor compound is extracted into chloroform and smelled after spotting on filter paper.

The conversion of the naturally occurring apocrine precursor to axillary malodor occurs within the bacterial cells. Extracts of bacteria are capable of converting the precursor to the malodor compound in an enzymatic process. The enzyme which is designated as the malodor-forming enzyme has been found to be a pyridoxal phosphate dependent amino acid lyase. The enzyme acts to cleave amino acids with the general structure HOOC—CH(NH$_2$)—CH(A)—X where A is H or CH$_3$ and X is S—R or O—R. The products of the reaction, when A is H, are pyruvate, ammonia, and XH. When A is CH$_3$, the products of the reaction are 2-ketobutyric acid, ammonia and XH.

The naturally occurring apocrine precursor to axillary malodor is a sulfur containing amino acid. It has now been found that a pleasant odor is produced if certain alternative substrates are provided in the axilla. Moreover, some compounds, for example, O-acyl serines of the invention, will not only produce a pleasant odor, but will also effectively block the production of axillary malodor when provided as an alternative substrate for the malodor-forming enzyme. In both instances, the malodor-forming enzyme cleaves the alternative substrate. Upon cleavage, the alternative substrates produce a pleasant odor.

Certain amino acids and amino acid analogues can serve as deodorants in this fashion, i.e., these amino acids and amino acid analogues serve as alternative substrates for the malodor-forming enzyme and upon cleavage produce a pleasant odor. As stated above, the malodor-forming enzyme cleaves amino acids and amino acid analogues having the general structure, HOOC—CH(NH$_2$)—CH(A)—X where A is H or CH$_3$ and X is S—R or O—R.

In the present invention, O-acylated serine and threonine derivatives are employed. The general structure of the O-acyl serines and threonines of the present invention is as follows:

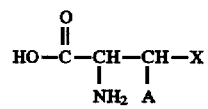

where A is H or CH$_3$ and X is O—C(O)—R. For the O-acyl serines, A is H and for the O-acyl threonines, A is CH$_3$. The O-acylated serine and threonine derivatives are in their L-enantiomeric forms. These derivatives comprise an R group which, upon cleavage, results in a compound R—COOH which produces a pleasant odor. That is, the R group may be any substituent which upon cleavage will produce an R—COOH compound which has a pleasant odor. The particular R group is not critical to the present invention so long as the resulting R—COOH compound is pleasant smelling.

One skilled in the art can readily determine whether an O-acyl serine or threonine derivative comprises an R group which, upon cleavage, results in a compound R—COOH which produces a pleasant odor. Compounds which will serve as alternative substrates for the malodor-forming enzyme can be assayed in the following manner. Bacterial cells of the Staphylococcus Haemolyticus strain are incubated with the alternative substrate compound in phosphate buffer at pH 6.8. After acidification, volatile compounds are extracted into chloroform and smelled after spotting on filter paper. If a pleasant odor is detected, the compound is an O-acyl serine or an O-acyl threonine of the invention.

More specifically, the R group is selected from the group consisting of ($C_1$–$C_{17}$) alkyl, ($C_1$–$C_{17}$) alkynyl, ($C_5$–$C_{12}$) cycloalkyl, and phenyl, each of which may be branched or unbranched, or optionally substituted with 1 or more substituents selected from the group consisting of hydroxyl, halo, cyano, amino, nitro, phenyl, mono- and di-alkylamines of from 1 to 10 carbon atoms in the amine group, alkoxy of from 1 to 10 carbon atoms, —SH, —SR where R is alkyl of from 1 to 10 carbon atoms, carboxyl, carboxyl esters of from 1 to 10 carbon atoms in the ester moiety, —$NR^1C(O)R^2$ where $R^1$ and $R^2$ are independently selected from the group consisting of hydrogen and alkyl of from 1 to 10 carbon atoms, heterocycles having from 2 to 6 carbon atoms, and 1 to 3 ring hetero atoms selected from the group consisting of nitrogen, oxygen and sulfur, a phenyl that is unsubstituted or substituted with one or more halo, hydroxyl, amino, nitro, amide, or carboxyl, or an aliphatic carbon chain of one to about 12 carbon atoms that is unsubstituted or substituted with one or more halo, hydroxyl, amino, nitro, amide, carboxyl, or phenyl that is unsubstituted or substituted with one or more halo, hydroxyl, amino, nitro, amide, or carboxyl.

Suitable substrates include, but are not limited to, compounds such as O-succinyl serine, O-benzoyl serine, O-phenylacetyl serine, O-malonyl serine, O-acetyl serine, O-oleoyl serine, O-palmitoyl serine, O-cinnamoyl serine, O-p-aminobenzoyl serine, O-lactoyl serine, O-salicyloyl serine, O-sarcosinoyl serine, O-2-ethyl hexanoyl serine, O-vanilloyl serine, O-phenylacetyl threonine, O-vanilloyl threonine, O-ethyl butyryl threonine, O-methyl valeryl threonine, O-cyclohexyl carboxyl threonine, O-cinnamoyl threonine, O-p-aminobenzoyl threonine, O-lactoyl threonine, O-salicyloyl threonine, O-sarcosinoul threonine, O-2-ethyl hexanoyl threonine and the like.

For example, the malodor-forming enzyme cleaves O-benzoyl serine (i.e., where X is O-benzoyl) to produce non-odorous benzoic acid. Similarly, the malodor-forming enzyme cleaves O-phenylacetyl threonine (i.e., where X is O-phenylacetyl) to produce phenylacetic acid, which has a pleasant odor. Suitable R groups of the O-acyl serines and O-acyl threonines of the present invention include —CH=CH—$C_6H_5$ which is cleaved to produce cinnamic acid; —$CH_2C_6H_5$ which is cleaved to produce phenylacetic acid; —$C_6H_4NH_2$ which is cleaved to produce p-aminobenzoic acid; —$CH(OH)CH_3$ which is cleaved to produce lactic acid; —$C_6H_4OH$ which is cleaved to produce salicylic acid; —$C_2H_4NH_2$ which is cleaved to produce sarcosine; and —$CH(C_2H_5)$—$(CH_2)_3$—$CH_3$ which is cleaved to produce 2-ethyl hexanoic acid.

Suitable O-acyl serines of the present invention can be prepared by the following procedure. Initially, protected serine is esterified with the desired R group compound, such as by esterification mediated by dicyclohexylcarbodiimide. The intermediate product may then be purified according to conventional purification techniques and recrystallized. The recrystallized intermediate product is then hydrogenated in the presence of an appropriate catalyst, e.g., palladium/carbon, to remove the protecting groups and yield the corresponding O-acyl serine.

Suitable O-acyl threonines of the present invention can be prepared by the following procedure. Initially, protected threonine is esterified with the desired R group compound, such as by esterification mediated by dicyclohexylcarbodiimide. The intermediate product may then be purified according to conventional purification techniques and recrystallized. The recrystallized intermediate product is then hydrogenated in the presence of an appropriate catalyst, e.g., palladium/carbon, to remove the protecting groups and yield the corresponding O-acyl threonine.

The presence of the O-acyl serines of the present invention in adequate quantities will compete with the natural precursor and at least reduce, if not almost entirely prevent the conversion of the natural precursor to the malodor compound.

Furthermore, when the O-acyl threonines of the invention and certain of the O-acyl serines are cleaved, pleasant odors are produced. These o-acylated serine derivatives are generally those in which the R group is an aromatic or branched chain aliphatic group. The acid that results from cleavage is pleasant smelling. The compound O-phenylacetyl serine or O-phenylacetyl threonine is converted to phenylacetic acid, a compound that smells of honey. O-phenylacetyl is thus an example of a preferred X group of the present invention.

The alternative substrates of the invention when present in moderate quantities compete with the natural precursor which is present in low quantities, typically about one nanomole/axilla. For the O-acyl serines of the invention, such competition almost completely prevents the malodor precursor from being converted. For both the O-acyl serines and threonines of the invention, such competition results in the conversion of the compounds to acids having a pleasant odor.

The concentration of O-acylated serine or threonine derivative employed in topical applications should be consistent with efficacy, economy and safety. The O-acylated serine and threonine derivatives of the present invention are employed in an amount sufficient to produce a pleasant odor. Alternatively, the O-acyl serines of the invention can be employed in an amount sufficient to produce a neutral odor. More specifically, the compounds of the invention are efficacious at concentrations between about 5 micromolar and about 500 millimolar, i.e., about 0.01% to about 10% by weight. The most preferred range is from about 50 micromolar to about 100 millimolar. This constitutes a weight percent of about 0.1% to about 2% by weight as the most preferred range of active ingredient.

Although deodorancy is the most important concern for the consumer of underarm products, many also choose a product with antiperspirant activity. Current antiperspirant compounds, which are aluminum salts, also function as deodorants by virtue of their germicidal properties. Thus, if desired, the deodorants of the present invention can be employed with the antiperspirant salts well known in the art. In such formulations, the O-acylated serine or threonine derivatives can be incorporated into a deodorant or antiperspirant formulation. In such case, the O-acylated serine or threonine derivative is added to a standard deodorant or antiperspirant formulation containing the antiperspirant salt in the same concentrations as set forth above. The antiperspirant salt may be employed in a perspiration reducing effective concentration, e.g., 6 to 30% or in a deodorant effective concentration, e.g., 1 to 6%.

The antiperspirant salt used in the present invention may be any of those which contain aluminum, either alone or in combination with other materials such as zirconium. Typical aluminum salts, although not all-inclusive, include: aluminum chlorohydrate; aluminum sesquichlorohydrate; aluminum dichlorohydrate; aluminum chlorohydrex PG or PEG; aluminum sesquichlorohydrex PG or PEG; aluminum dichlorohydrex PG or PEG; aluminum zirconium trichlorohydrate; aluminum zirconium tetrachlorohydrate; aluminum zirconium tetrachlorohydrex PG or PEG; aluminum zirconium pentachlorohydrate; aluminum zirconium octachlorohydrate; aluminum zirconium trichlorohydrex-gly; aluminum zirconium tetrachlorohydrex-gly; aluminum zirconium pentachlorohydrex-gly; aluminum zirconium octachlorohydrex-gly; aluminum zirconium chloride; aluminum zirconium sulfate; potassium aluminum sulfate; sodium aluminum chlorohydroxylactate; and aluminum bromohydrate.

In general, the active antiperspirant salt is present in the same amounts at which such materials are employed in prior art compositions. As a general rule, such compositions contain from about 3% to about 30%, preferably from about 10% to about 25%, of the active antiperspirant salt component.

In order to further illustrate the present invention and the advantages thereof, the following specific examples are given. It is understood that these examples are intended only to be illustrative without serving to limit the scope of the present invention.

EXAMPLES

Example 1

Preparation of O-phenyl acetyl Serine

Step 1

6.01 g (0.043 mol) of phenyl acetic acid was dissolved in 200 mL of methylene chloride. 14.03 g (0.043 mol) of carbobenzyloxy-serine-benzyl ester ("Cbz-serine-benzyl ester") and 0.382 g (0.013 mol) of dimethyl amino pyridine ("DMAP") were then added. The resulting mixture was cooled on an ice bath. 8.9 g (0.043 mol) of dicyclohexylcarbodiimide ("DCC") was next added. This mixture was kept on an ice bath for 5 minutes, then the ice was removed and the mixture stirred at room temperature under $N_2$ for 4 hours.

The mixture was then filtered to remove any precipitated dicyclohexyl urea. The mixture was next concentrated to dryness, then re-dissolved in methylene chloride and filtered to remove any new precipitate. This mixture was then washed twice with 1 N HCl then once with 0.1 N NaOH. The organic layer was dried over $MgSO_4$ and concentrated in vacuo. The crude product was recrystallized from 2-propanol to give carbobenzyloxy-phenylacetyl-serine-benzyl ester as white needles, m.p. 59°–60° C.

Step 2

11.1 g (0.25 mol) of the protected amino acid, carbobenzyloxy-phenylacetyl-serine-benzyl ester, obtained in Step 1 was placed in a large flask and dissolved in 350 mL of methanol with stirring. Stirring was stopped, and 2.9 g of the 10% Pd/carbon catalyst added slowly. The vessel was purged with $H_2$ for 1 minute. The reaction was then stirred under $H_2$ (1 atmosphere) overnight. The reaction mixture was filtered through a pad of Celite, the pad was rinsed with MeOH, and the combined filtrate and rinsings were concentrated in vacuo to give the product O-phenyl acetyl serine as a white solid, m.p. 90°–92° C.

Example 2

Step 1

1 g (2.9 mmole) N-Carbobenzyloxy-threonine-benzyl ester (Cbz-Thr-OBz) was dissolved in dry methylene chloride (20 mL). 0.4 g of phenyl acetic acid (2.9 mmole) was added, followed by 10 g of the catalyst 4-dimethylaminopyridine ("DMAP"). The mixture was cooled to 0° C. on an ice bath under $N_2$ and 0.61 g (2.9 mmole) of dicyclohexylcarbodimide ("DCC") was added. Stirring was continued at 0° C. for 5 minutes, then at room temperature for 3 hours.

The precipitated dicyclohexylureas was removed by filtration and the filtrate was concentrated in vacuo. The residue was suspended in acetone and re-filtered. The filtrate was again concentrated in vacuo. The residue was taken up in 20 mL of methylene chloride, washed with 1 n hydrochloric acid (2×15 mL), 10 mL of 10% citric acid and 15 ml of 0.1 N sodium hydroxide, dried over $MgSO_4$, and concentrated to leave the product as an oil. The produce was crystallized from isopropyl alcohol to give Cbz-(O-phenylacetyl)threonine benzyl ester as white needles.

Step 2

350 mg (0.8 mmole) of Cbz-(O-phenylacetyl)threonine benzyl ester was dissolved in 15 mL of methanol. Stirring was stopped and 99 mg (28 weight percent relative to substrate) of a 10% palladium/carbon catalyst was added in small portions. The mixture was flushed with hydrogen for a few seconds and the flask was fitted with a hydrogen filled balloon. Stirring was then restarted, the ice bath removed, and the reaction was stirred at room temperature for 3 hours.

The reaction mixture was next filtered to remove the catalyst. The filtrate was concentrated in vacuo. Upon trituration of the residue with water, the product, phenylacetyl threonine, was isolated as a white solid. The product had a melting point of 118°–120° C.

Example 3

Evaluation of phenylacetyl threonine in an in vitro sniff test

Phenylacetyl threonine was assayed in a sniff test with whole Staph. Haemolyticus cells. To do the assay, 50 µL of a suspension of cells in 50 mM potassium phosphate (pH 6.8) was aliquotted into a ½ dram glass vial. A stock solution of the phenylacetyl threonine in the same buffer was added to the cells, followed by buffer to a volume of 100 µL. The mixture was incubated at 37° for 45 minutes. The reaction was stopped by the addition of 10 µL of 1 N hydrochloric acid. The sample was then extracted with 200 µL $CHCl_3$. At least 15 minutes at room temperature was allowed for partition of the organics into the $CHCl_3$ layer. The organic extract was then analyzed in one of two ways. first, small aliquots from the organic layer were spotted onto bibulous paper. After the chloroform had evaporated, the paper was sniffed by judges to identify any fragrance. The compound was found to have produced a honey-rose fragrance. An aliquot could also be taken and analyzed by GC/MS for presence of the product phenylacetic acid to determine whether the malodor producing enzyme had cleaved the phenylacetyl threonine.

Example 4

Evaluation of O-acyl serines that produce neutral or odorless products

As a representative of the class, O-succinyl serine was evaluated and was found to be effective as a substrate of the malodor enzyme at concentrations of 1 millimolar and above. When tested as described in Example 3, above, for the ability to block malodor formation by bacterial cells from sterilized apocrine secretions, the minimum concentration needed for complete inhibition was 150 millimolar.

Example 5

Evaluation of O-acyl serines that produce a pleasant odor

O-phenylacetyl serine was tested as described in Example 3, above, for the ability to inhibit malodor formation by bacterial cells from sterilized apocrine secretions, while producing in its place a pleasant odor. The compound blocked malodor production at a concentration of 25 millimolar while producing a pleasant, honey-like fragrance.

Examples 6–11

These examples illustrate six deodorant/antiperspirant formulations comprising the compounds of the present invention.

Example 6

| Deodorant Stick | |
|---|---|
| Ingredient | % by weight |
| propylene glycol | 78 |
| sodium stearate C-1 | 7.9 |
| fragrance | 0.1 |
| water | 13 |
| O-phenylacetyl serine | 1 |

Procedure: Mix propylene glycol and sodium stearate C-1 at room temperature and stir. Increase the temperature to about 70° C. and continue agitation to obtain a clear and uniform solution. Add the water followed by the O-phenylacetyl serine. Lower the temperature to 55° C. and add the fragrance. Pour into molds and cool to room temperature.

Example 7

| Deodorant Roll-On Emulsion | |
|---|---|
| Ingredient | % by weight |
| hydrogenated palm oil glycerides and sodium cetyl sulfate | 3.0 |
| steareth-7 | 1.0 |
| octyldodecanol | 4.0 |
| glyceryl laurate | 2.0 |
| octyl palmitate | 4.0 |
| dimethicone | 1.0 |
| propylparaben | 0.1 |
| methylparaben | 0.2 |
| imidazolidinyl urea | 0.3 |
| glycerin | 5.0 |

| -continued | |
|---|---|
| Deodorant Roll-On Emulsion | |
| Ingredient | % by weight |
| allantoin | 0.5 |
| PEG-35 lanolin | 0.5 |
| fragrance | 0.3 |
| 2 wt. % O-benzoyl serine in 80% propylene glycol/20% water at neutral pH | 78.1 |

Procedure: Mix and stir the ingredients except the fragrance at 80° C. Decrease the temperature to 40° C. and add the fragrance. Decrease the temperature to room temperature.

Example 8

| Aerosol Deodorant | |
|---|---|
| Ingredient | % by weight |
| zinc phenolsulfonate | 1.7 |
| quaternium 18 hectorite | 1.0 |
| dioctyl succinate | 10.0 |
| SDA 40 ethanol, anhydrous | 20.0 |
| fragrance | 0.1 |
| 1 wt. % O-succinyl serine in 50% ethanol/water at neutral pH | 10.0 |
| propellant | 57.2 |

Procedure: Dissolve all ingredients in the alcohol, add the propellant, and cold or pressure fill.

Example 9

| Roll-On Antiperspirant and Deodorant | |
|---|---|
| Ingredient | % by weight |
| PPG-15 stearyl ether | 4.0 |
| steareth-21 | 0.6 |
| steareth-2 | 2.6 |
| aluminum zirconium pentachlorohydrate, 10:1 (a 25% solution) | 32.0 |
| fragrance | 0.1 |
| 1.8 wt % O-oleoyl serine in 80% propylene glycol/water at neutral pH | 60.7 |

Procedure: Mix all the ingredients except the fragrance at 70° C. with agitation. Add the fragrance at 45° C. Stir and cool to room temperature.

Example 10

| Aerosol Antiperspirant and Deodorant | |
|---|---|
| Ingredient | % by weight |
| O-palmitoyl serine | 1.0 |
| isopropyl myristate | 13.4 |
| aluminum chlorohydrate | 10.0 |
| quaternium-18 hectorite | 0.8 |
| SDA 40 ethanol, anhydrous | 0.8 |
| fragrance | 0.1 |
| propellant | 73.9 |

Procedure: Mix the isopropyl myristate and quaternium-18 hectorite together for 30 minutes with an Eppenbach Homomixer. Add aluminum chlorohydrate and mix 15 minutes. Add the O-palmitoyl serine and SDA 40 and mix 10 minutes. Homogenize the suspension using a Manton-Gaulin homogenizer set at 6000 psi. Add fragrance and mix on a Hobart Mixer set at moderate speed. Mix 10 minutes. Charge with propellant.

Example 11

Stick Antiperspirant and Deodorant

| Ingredient | % by weight |
|---|---|
| aluminum chlorohydrate | 16.0 |
| SDA 40 ethanol, anhydrous | 30.0 |
| sorbitol, 70% | 3.0 |
| sodium stearate C-1 | 5.0 |
| sodium ceteth-13 carboxylate | 3.0 |
| stearyl alcohol | 1.0 |
| cyclomethicone | 15.0 |
| fragrance | 0.1 |
| 2 wt. % O-malonyl serine in 80% propylene glycol/water at neutral pH | 26.9 |

Procedure: Mix the aluminum chlorohydrate, SDA 40 ethanol and the O-malonyl serine and heat to 65° C. Add sorbitol and then sodium stearate C-1 and sodium ceteth-13 carboxylate, and mix until a complete solution is obtained. Add the remaining ingredients and mix for 5 minutes. Cool to 50° C. and add to containers.

Other objects, features and advantages of the present invention will become apparent from the foregoing detailed description and accompanying examples. It should be understood, however, that the detailed description and specific examples, while indicating various embodiments of the invention, are given by way of illustration only, since various changes and modifications within the spirit and scope of the invention will become apparent to those skilled in the art from this detailed description.

What is claimed is:

1. A deodorant composition comprising, in a dermatologically acceptable vehicle, about 0.01% to about 10% by weight of a compound of the structure

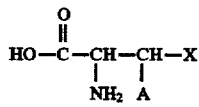

where A is H or $CH_3$ and X is O—C(O)—R, and R is a substituent such that RCOOH, formed by cleavage of said compound by axillary bacteria, has a neutral or pleasant odor.

2. The deodorant composition of claim 1, wherein R is a substituent such that RCOOH, formed by cleavage of said compound by axillary bacteria, has a pleasant odor.

3. The deodorant composition of claim 1, wherein R is selected from the group consisting of ($C_1$-$C_{17}$) alkyl, ($C_1$-$C_{17}$) alkynyl, ($C_5$-$C_{12}$) cycloalkyl, and phenyl, each of which may be branched or unbranched, or optionally substituted with 1 or more substituents selected from the group consisting of hydroxyl, halo, cyano, amino, nitro, phenyl, mono- and di- alkylamines of from 1 to 10 carbon atoms in the amine group, alkoxy of from 1 to 10 carbon atoms, —SH, —SR where R is alkyl of from 1 to 10 carbon atoms, carboxyl, carboxyl esters of from 1 to 10 carbon atoms in the ester moiety, —$NR^1C(O)R^2$ where $R^1$ and $R^2$ are independently selected from the group consisting of hydrogen and alkyl of from 1 to 10 carbon atoms, heterocycles having from 2 to 6 carbon atoms, and 1 to 3 ring hetero atoms selected from the group consisting of nitrogen, oxygen and sulfur, a phenyl that is unsubstituted or substituted with one or more halo, hydroxyl, amino, nitro, amide, or carboxyl, or an aliphatic carbon chain of one to about 12 carbon atoms that is unsubstituted or substituted with one or more halo, hydroxyl, amino, nitro, amide, carboxyl, or phenyl that is unsubstituted or substituted with one or more halo, hydroxyl, amino, nitro, amide, or carboxyl.

4. The deodorant composition of claim 1, wherein said compound is O-succinyl serine, O-benzoyl serine, O-phenylacetyl serine, O-malonyl serine, O-acetyl serine, O-oleoyl serine, O-palmitoyl serine, O-cinnamoyl serine, O-p-aminobenzoyl serine, O-lactoyl serine, O-salicyloyl serine, O-sarcosinoyl serine, O-2-ethyl hexanoyl serine, O-vanilloyl serine, O-phenylacetyl threonine, O-vanilloyl threonine, O-ethyl butyryl threonine, O-methyl valeryl threonine, O-cyclohexyl carboxyl threonine, O-cinnamoyl threonine, O-p-aminobenzoyl threonine, O-lactoyl threonine, O-salicyloyl threonine, O-sarcosinoyl threonine or O-2-ethyl hexanoyl threonine.

5. The deodorant composition of claim 4, wherein said compound is O-phenylacetyl threonine, O-vanilloyl threonine, O-ethyl butyryl threonine, O-methyl valeryl threonine, O-cyclohexyl carboxyl threonine, O-cinnamoyl threonine, O-p-aminobenzoyl threonine, O-lactoyl threonine, O-salicyloyl threonine, O-sarcosinoyl threonine or O-2-ethyl hexanoyl threonine.

6. The deodorant composition of claim 1, comprising about 0.1% to about 2% by weight of said compound.

7. The deodorant composition of claim 1, wherein said compound is present at a concentration of between about 5 micromolar and about 500 millimolar.

8. The deodorant composition of claim 1, wherein said compound is present at a concentration of between about 50 micromolar to about 100 millimolar.

9. The deodorant composition of claim 1, further comprising an antiperspirant salt.

10. A method of producing a pleasant odor in the axilla comprising applying to skin the deodorant composition of claim 1.

11. A method of reducing malodor in the axilla comprising applying to skin the deodorant composition of claim 1.

12. A method of producing a pleasant odor in the axilla comprising applying to skin the deodorant composition of claim 2.

* * * * *

UNITED STATES PATENT AND TRADEMARK OFFICE
CERTIFICATE OF CORRECTION

PATENT NO.   :   5,800,804
DATED        :   September 1, 1998
INVENTOR(S)  :   Judith Wolfe Laney It is certified that error appears in the above-identified patent and that said Letters Patent is hereby corrected as shown below:

Cancel claim 4;

claim 5, line 1, change "4" to --1--.

Signed and Sealed this

Twenty-ninth Day of December, 1998

Attest:

BRUCE LEHMAN

*Attesting Officer*          *Commissioner of Patents and Trademarks*